United States Patent [19]

Alvarez

[11] Patent Number: 5,061,689
[45] Date of Patent: Oct. 29, 1991

[54] ZINC BACITRACIN CONTAINING WOUND DRESSING

[75] Inventor: Oscar M. Alvarez, East Brunswick, N.J.

[73] Assignee: Bioderm, Inc., Plainsboro, N.J.

[21] Appl. No.: 946,311

[22] Filed: Dec. 24, 1986

[51] Int. Cl.$^5$ .................... A61K 37/00; A61K 37/14
[52] U.S. Cl. ...................................... 514/6; 424/445; 424/447; 514/10
[58] Field of Search .................... 424/445, 447; 514/6, 514/10

[56] References Cited

U.S. PATENT DOCUMENTS 2,809,149 10/1957 Cusumano ..................... 514/10 X
3,419,006 12/1968 King ............................. 424/445 X

OTHER PUBLICATIONS

Physicians' Desk Reference, 26th ed., 1972, p. 690 ("Neo-Polycin").
Physicians' Desk Reference, pp. 303, 764, 765, Edition 35, 1981, Charles E. Baker, Jr., Publisher.
The Pharmacological Basis of Therapeutics, pp. 1293, 1294, Edition 4, 1970, Edited by Louis S. Goodman, M.A., M.D., D. Sc. (Hon.) and Alfred Gilman, Ph.D.

*Primary Examiner*—Leonard Schenkman
*Attorney, Agent, or Firm*—Brumbaugh, Graves, Donohue & Raymond

[57] ABSTRACT

Bacitracin zinc is effective to promote regenerative healing when topically applied to wounds in concentrations from about 5% to 8%. The bacitracin zinc can be applied in a hydrophilic or hydrophobic carrier, and is advantageously impregnated in an absorbent pad.

13 Claims, No Drawings

ZINC BACITRACIN CONTAINING WOUND DRESSING

BACKGROUND OF THE INVENTION

The present application relates to a method and wound dressing for promoting epidermal resurfacing of wounds which involves the use of bacitracin zinc.

Bacitracin is a polypeptide antibiotic produced by the Tracy-I strain of *Bacillus subtilis*. Bacitracin zinc is the zinc salt of the antibiotic.

It is known to utilize bacitracin zinc in dermatological ointments in combination with other antibiotics to treat topical skin infections such as infected burns, skin grafts, surgical incisions, otitis externa, primary pyoderma, secondary infected dermatoses and infected traumatic lesions. The ointment is also recommended for prophylactic use to prevent infection of minor injuries which could retard healing.

The known ointments, such as Neosporin ®, contain about 400 units of bacitracin zinc, with a potency of not less than 40 units per mg, per gram of ointment. Thus, known ointments contain less than about 1% bacitracin zinc.

SUMMARY OF THE INVENTION

Bacitracin zinc has been found to be an effective agent for promoting epidermal resurfacing when applied in an ointment base at concentrations of about 5% to 8%. Preferably, the bacitracin zinc ointment is impregnated into a layer of reticulated foam which is used as a wound dressing. This layer of impregnated foam may also be covered with a semipermeable occlusive film such as polyurethane.

DETAILED DESCRIPTION OF THE INVENTION

According to the invention, epidermal resurfacing of wounds can be enhanced by treating the wound with a composition comprising bacitracin zinc in a pharmaceutically acceptable carrier. Preferably, the composition will contain 5% to 8% bacitracin zinc, as higher levels tend in inhibit rather than promote healing. Most preferably the composition will contain about 7% bacitracin zinc.

The preferred carriers are hydrophilic ointment bases which are known to persons skilled in the art. Suitable carrier materials include carboxymethyl cellulose, polyethylene oxide, polyethylene glycol, marine colloids such as carrageenan gums, and sodium or calcium alginate.

A specific example of a suitable hydrophilic ointment containing bacitracin zinc is as follows:

| | |
|---|---|
| Carbomer 940 | 5 g |
| Methyl Paraben | 0.75 g |
| NaOH (1N) | 25 g |
| H$_2$O + bacitracin zinc | q.s 500 g |

In making the ointment, the water and bacitracin zinc are preferably combined first, and then added to the other ingredients.

Alternatively, the bacitracin zinc can be suspended in a hydrophobic carrier. Suitable hydrophobic carriers include petrolatum, petroleum distillates, mineral oil, polyethylene glycol, lanolin/petrolatum, triglycerides, and animal derived oils, or mixtures thereof.

The bacitracin zinc ointment can be applied directly to the wound. Preferably, however, the ointment is contained within a pad, such as of guaze or foam. Advantageously, a layer of reticulated foam which has been impregnated with the bacitracin zinc composition can be used to apply the composition to a wound. The impregnated foam dressing can include means for affixing the dressing to the wound area, or it can be affixed by other known means such as adhesive tape. The purpose of the foam layer is to provide controlled delivery of the bacitracin zinc, as well as a degree of padding. One skilled in the art will recognize that other means of providing controlled delivery could be used as well.

In a preferred embodiment according to the invention, a semipermeable occlusive film is applied over the top of the bacitracin zinc impregnated pad. This can lead to a 20% further enhancement in the rate of healing over bacitracin zinc used along. Suitable film materials include polyurethane, copolyesters, butadiene copolymers and coagulated PTFE films.

EXAMPLE I

To test the effect of bacitracin zinc on epidermal resurfacing, approximately 60 rectangular wounds measuring 7 mm wide, 10 mm long, and 0.5 mm deep were made in each of eighteen white Yorkshire pigs in the paravertebral and thoracic areas with a Castroviejo keratome. The electrokeratome was fitted with a razor blade modified so that the cutting edge was reduced to 7 mm. The wounds were separated from one another by at least 15 mm of normal skin.

On each of the experimental animals, approximately one third of the wounds were assigned to one of three treatment groups: (1) control (no treatment), (2) vehicle alone, (low melting point petrolatum 3.0 g) or (3) bacitracin zinc (either 1%, 2.5%, 5%, 7%, 10% or 20% in 3.0 g). A total of 99 wounds on 3 pigs were treated with each of the varying bacitracin zinc combinations. Vehicle was applied to 594 wounds in 18 animals. The other 594 wounds were the untreated controls.

The bacitracin zinc was applied in impregnated foam shortly (within 5 minutes) after wounding on day 0 and once daily thereafter for 7 days. In order to rule out the possibility that wounds made in different anatomical regions heal at different rates the regions used for each treatment group varied for each animal.

Two days after wounding and each day thereafter some of the wounds with surrounding normal skin were excised from each treatment group. The excisions were made with a Castroviejo keratome fitted with a 22 mm blade, set to cut at a depth of 0.7 mm. After incubating the specimens in 2N sodium bromide at 37° C. for three hours, the epidermis was separated from the dermis and the epidermal sheet (22 sq mm) was assessed for re-epithelialization as previously described. Briefly, this method is a macroscopic examination of the separated epidermis for defects. Defects are visualized as holes in the separated epidermal sheet or as a lack of epidermal continuum in the area that contain the wound. The wound is considered re-epithelialized if there are no defects in the epidermis and not re-epithelialized if there are one or more defects.

The effects of different bacitracin zinc concentrations impregnated in a foam and the effects of the vehicle alone on epidermal wound healing are presented in Table 1. The rate of wound re-epithelialization was significantly greater in the 7% bacitracin zinc treated wounds when compared with both untreated and vehicle treated wounds. There was no significant difference between the other concentrations of bacitracin zinc and the ointment vehicle treated wounds. All vehicle treated wounds healed significantly faster than untreated control wounds.

The time needed for 50% of the wounds in each experimental animal to heal HT$_{50}$) has been estimated from curves generated by probit analysis of the data presented in Table I. The HT$_{50}$ values and the relative rate of healing are compared in Table II. Wounds treated with 7% bacitracin zinc healed 46% more rapidly than untreated wounds and 28% faster than wounds treated with the ointment alone. Vehicle treated wounds healed approximately 25% faster than wounds left open to the air.

EXAMPLE II

Further tests were conducted to determine the effect of bacitracin zinc covered with an occlusive film. The wounds in these were treated according to one of four treatment regiments: (1) untreated; (2) polyurethane film; (3) 7% bacitracin zinc ointment; and (4) 7% bacitracin zinc ointment plus polyurethane film. The methodology employed was substantially the same as in Example I.

The results of these tests are summarized in Tables 3 and 4. Wounds treated with bacitracin zinc alone healed about 4% faster than those treated with the polyurethane film alone, and about 24% faster than the untreated controls. The wounds treated with combination of bacitracin zinc and the polyurethane film healed 25% faster than those treated with the polyurethane film alone, and 40% faster than the untreated controls.

EXAMPLE III

To more accurately assess the effective range of bacitracin concentrations, bacitracin zinc containing ointments were prepared with concentrations ranging from 3% to 9%. The methodology employed was substantially the same as in Example I.

The results of these tests are summarized in Table 5. From the results it can be seem that some enhancement of healing is observed at a concentration of 4%. Preferred healing is observed at higher concentrations, particularly in the range of 6.5%-7.5%.

TABLE 1
EFFECT OF BACITRACIN ZINC IMPREGNATED FOAM DRESSING ON EPIDERMAL WOUND HEALING

| TREATMENT | 2$^a$ | 3 | 4 | 5 | 6 | 7 |
|---|---|---|---|---|---|---|
| 1% Bacitracin | 0 | 0 | 40$^c$ | 58$^c$ | 95 | 100 |
| Zinc | | | | | | |
| 2.5% | 0 | 0 | 36$^c$ | 60$^c$ | 96 | 100 |
| 5.0% | 0 | 11 | 54$^c$ | 77$^c$ | 95 | 100 |
| 7.0% | 0 | 36$^b$ | 70$^{bc}$ | 98$^{bc}$ | 100$^c$ | 100 |
| 10.0% | 0 | 2 | 33$^c$ | 66$^c$ | 92 | 100 |
| 20.0% | 0 | 0 | 42$^c$ | 58$^c$ | 96 | 100 |
| Vehicle | 0 | 3 | 45$^c$ | 66 | 96 | 100 |
| Untreated | 0 | 0 | 0 | 33 | 74 | ND |

$^a$values are % of wounds healed
$^b$p 0.05 compared with vehicle
$^c$p 0.05 compared with untreated
ND not determined

TABLE 2
COMPARISON RATES OF HEALING

| TREATMENT | HT$_{50}$(days)$^a$ | Compared with Vehicle (%) | Compared with Untreated (%) |
|---|---|---|---|
| 1% Bacitracin | 4.5 | 0 | +23 |
| Zinc | | | |
| 2.5% | 4.4 | 2 | +25 |
| 5.0% | 3.9 | 13 | +34 |
| 7.0% | 3.2 | 28* | +46* |
| 10.0% | 4.8 | −6 | +19 |
| 20.0% | 4.8 | −6 | +19 |
| Vehicle | 4.5 | — | +24 |
| Untreated | 5.9 | −31 | — |

$^a$Time in days for 50% of wounds to be completely healed.
*P 0.05 compared to untreated.

TABLE 3
EFFECT OF A TOPICALLY APPLIED 7% BACITRACIN ZINC OINTMENT WITH AND WITHOUT OCCLUSION ON THE HEALING OF DEEP PARTIAL THICKNESS WOUNDS

| TREATMENT | 2* | 3 | 4 | 5 | 6 | 7 |
|---|---|---|---|---|---|---|
| BAC. ZN/ | 0$^a$ | 38$^{bc}$ | 66$^{bc}$ | 100$^c$ | 100 | 100 |
| Polyurethane$^d$ | | | | | | |
| BAC. ZN | 0 | 19$^c$ | 42$^c$ | 77$^c$ | 92 | 100 |
| POLYURETHANE$^d$ | 0 | 10 | 35$^c$ | 75$^c$ | 100 | 100 |
| UNTREATED | 0 | 0 | 0 | 30 | 75 | 88 |

*days after wounding
$^a$values are % of wounds healed
$^b$p < 0.5 compared with BAC Zn along and polyurethane along
$^c$p < 0.5 compared with untreated
$^d$polyurethane occlusion, 1 mil thick with perimeter adhesive (Blisterfilm ™)

TABLE 4
COMPARATIVE RATE OF HEALING

| TREATMENT | HT$_{50}$ (days)$^a$ | COMPARED WITH PU FILM | COMPARED WITH UNTREATED |
|---|---|---|---|
| BAC. ZN/ POLYURETHANE | 3.2 | +25 | +40 |
| BAC. ZN | 4.1 | +4 | +24 |
| POLYURETHANE | 4.3 | — | +20 |
| UNTREATED | 5.4 | −25 | — |

$^a$time in days for 50% of wounds to be completely healed

TABLE 5
EFFECT OF TOPICALLY APPLIED BACITRACIN ZINC ON THE HEALING OF PARTIAL THICKNESS WOUNDS

| CONCENTRATION BACITRACIN ZINC (%) | DAYS AFTER WOUNDING | | | | |
|---|---|---|---|---|---|
| | 2 | 3 | 4 | 5 | 6 | 7 |
| 3.0 | 0$^a$ | 0 | 33 | 55 | 90 | 100 |
| 4.0 | 0 | 5 | 45 | 60 | 96 | 100 |
| 5.0 | 0 | 9 | 48 | 71 | 95 | 100 |
| 5.5 | 0 | 15 | 55 | 75 | 98 | 100 |
| 6.0 | 0 | 20 | 59 | 78 | 98 | 100 |
| 6.5 | 0 | 33 | 65 | 88 | 100 | 100 |
| 7.0 | 0 | 40 | 70 | 96 | 100 | 100 |
| 7.5 | 0 | 38 | 68 | 92 | 98 | 100 |
| 8.0 | 0 | 12 | 59 | 75 | 90 | 100 |
| 9.0 | 0 | 4 | 33 | 66 | 90 | 100 |

$^a$% of wounds healed

I claim:

1. A wound dressing comprising a layer of an impregnatable material, said material being impregnated with a composition comprising 5% to 8% bacitracin zinc in a pharmaceutically acceptable carrier.

2. A wound dressing according to claim 1, wherein the composition comprises 6.5% to 7.5% bacitracin zinc.

3. A wound dressing according to claim 1, wherein the impregnatable material comprises reticulated foam.

4. A wound dressing according to claim 3, further comprising a semipermeable occlusive film affixed to one side of the reticulated foam layer.

5. A wound dressing according to claim 4, further comprising means for affixing the dressing to a wounded area.

6. A wound dressing according to claim 4, wherein the film is polyurethane.

7. A wound dressing according to claim 6, wherein the composition comprises about 6.5% to 7.5% bacitracin zinc.

8. A method for enhancing epidermal resurfacing of a wound comprising treating the wound with a composition comprising 5% to 8% of bacitracin zinc in a pharmaceutically acceptable carrier.

9. The method of claim 8, wherein the composition is impregnated in a reticulated foam.

10. The method of claim 8, wherein the carrier is a hydrophilic ointment.

11. A method for enhancing epidermal resurfacing of a wound, comprising treating the wound with a composition comprising about 6.5 to 7.5% bacitracin zinc in a pharmaceutically acceptable carrier, said composition being impregnated in a reticulated foam.

12. The method of claim 11, further comprising the step of covering the impregnated foam with a semipermeable occlusive film.

13. The method of claim 12, wherein the film is polyurethane.

* * * * *